United States Patent [19]

Krause

[11] 4,415,505

[45] Nov. 15, 1983

[54] PROCESS FOR MAKING ALKYL OR ARYLTHIOPHOSPHONIC ACID

[75] Inventor: Werner Krause, Hürth, Fed. Rep. of Germany

[73] Assignee: Hoechst Aktiengesellschaft, Fed. Rep. of Germany

[21] Appl. No.: 400,892

[22] Filed: Jul. 22, 1982

[30] Foreign Application Priority Data

Aug. 7, 1981 [DE] Fed. Rep. of Germany ....... 3131249

[51] Int. Cl.³ .............................................. C07F 9/42
[52] U.S. Cl. ............................................... 260/543 P
[58] Field of Search ......................... 260/543 P, 543 R

[56] References Cited

U.S. PATENT DOCUMENTS 2,662,917 12/1953 Jensen ............................. 260/543 P
4,000,190 12/1976 Uhing et al. ..................... 260/543 P
4,130,583 12/1978 Uhing et al. ..................... 260/543 P
4,213,922 7/1980 Maier ............................. 260/543 P

FOREIGN PATENT DOCUMENTS 2064774 10/1969 France ............................ 260/543 P
54-6046861 9/1979 Japan ............................. 260/543 R Primary Examiner—Paul J. Killos
Attorney, Agent, or Firm—Connolly and Hutz

[57] ABSTRACT

The disclosure relates to a process for making alkyl or arylthiophosphonic acid dichlorides by reacting alkyl or aryldichlorophosphanes with sulfur at a temperature above the melting point of sulfur and in the presence of a catalyst. More particularly, the reaction is effected at a temperature between the melting point of sulfur and the boiling point of the resulting alkyl or arylthiophosphonic acid dichloride and in the presence of a catalyst of the following general formula I or II

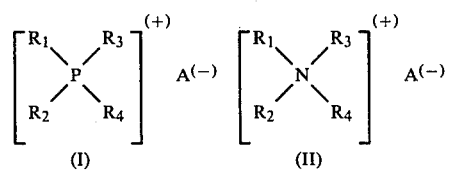

in which $R_1$, $R_2$, $R_3$ and $R_4$ stand for identical or different alkyl, aryl, alkaryl, or aralkyl groups having from 1 to 22 carbon atoms and A stands for the anionic group of an organic or inorganic acid.

7 Claims, No Drawings

PROCESS FOR MAKING ALKYL OR ARYLTHIOPHOSPHONIC ACID

The present invention relates to a process for making alkyl or arylthiophosphonic acid dichlorides by subjecting alkyl or aryldichlorophosphanes to catalytic reaction with sulfur.

It has already been described (cf. Houben-Weyl, Methoden der organischen Chemie, volume XII/1, page 555) that alkyl or arylthiophosphonic acid dichlorides can be made by reacting suitable alkyl or aryldichlorophosphanes with sulfur under the catalytic action e.g. of $AlCl_3$, $FeCl_3$ or $ZnCl_3$. The continuous manufacture of methanethiophosphonic acid dichloride has been described in Fench Pat. No. 2 064 774, wherein methyldichlorophosphane is reacted with sulfur at about 150° C. with addition of 4 weight % $AlCl_3$, based on $CH_3PCl_2$. After distillative separation of the product from the reaction mixture, the yield is about 92% of the theoretical. While the black-colored distillation residue can under circumstances be used again in further reactions, the fact remains that its catalytic activity decreases rapidly so that it is invariably necessary for further quantities e.g. of $AlCl_3$ to be added to the reaction batch. As an inevitable result of this, increased quantities of distillation residue which, for reasons of environmental protection, can be disposed of with considerable expense only, are obtained.

We have now unexpectedly found that substituted phosphonium or ammonium salts equally catalyze the reaction of alkyl or aryldichlorophosphanes with sulfur, the salts retaining their catalytic activity during the reaction. In other words, it is just necessary for the catalyst to be added once to the initial batch, at the onset of the reaction, the next batches having the distillation residue originating from the respective preceding batch added thereto.

More specifically, the invention relates to a process for making alkyl or arylthiophosphonic acid dichlorides by reacting alkyl or aryldichlorophosphanes with at least stoichiometric proportions of sulfur at a temperature above the melting point of sulfur and in the presence of a catalyst, and separating the resulting alkyl or arylthiophosphonic acid dichloride from the reaction mixture after the reaction has been terminated, which comprises: effecting the reaction at a temperature between the melting point of sulfur and the boiling point of the resulting alkyl or arylthiophosphonic acid dichloride and in the presence of a catalyst of the following general formula I or II

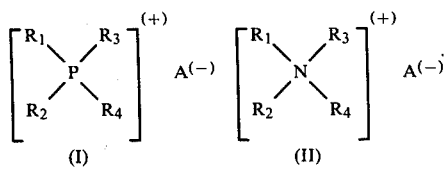

in which $R_1$, $R_2$, $R_3$ and $R_4$ stand for identical or different alkyl, aryl, alkaryl or aralkyl groups having from 1 to 22 carbon atoms and A stands for the anionic group of an organic or inoganic acid, the catalyst being used in a proportion of 0.01 to 5 weight %, based on the quantity of the phosphane component; terminating the reaction and separating the alkyl or arylthiophosphonic acid dichloride from the reaction mixture; and using resulting catalyst-containing residue in further reactions of alkyl or aryldichlorophosphanes with sulfur.

The alkyl or aryldichlorophosphanes as well as the thiophosphonic acid dichlorides obtainable by the process of this invention preferably contain 1 to 8 carbon atoms.

The feed materials comprise sulfur and preferably methyl, ethyl or phenyldichlorophosphanes, the reaction being preferably effected at a temperature of 130° up to 170° C. The reaction should preferably be accelerated using tetraalkylammonium or tetraalkylphosphonium chloride, bromide, sulfate, nitrate or acetate as the catalyst.

A preferred feature of the present process provides for the phosphane component to be introduced portionwise into a mixture of sulfur and catalyst and, after the phosphane addition is complete, for the reaction mixture to be subjected to a post-reaction over a period of 5 to 60 minutes. The catalyst should preferably be used in a proportion of 0.05 to 2 weight %, based on the quantity of the phosphane component. The use of more catalyst could not be found to result in adverse effects; it should however be avoided for reasons of economy and as being redundant. Under the action of the catalyst, the reaction of this invention proceeds rapidly and completely. After the reaction has been terminated, the thiophosphonic acid dichloride is distillatively removed from the crude reaction mixture. The catalyst is retained in the distillation residue which is admixed with sulfur and used in the next batch.

The phosphonium and ammonium salts, respectively, suggested to be used as catalyst in accordance with this invention compare favorably with the metal chlorides used heretofore inasmuch as hydrolytic action does not result in the phosphonium or ammonium salts becoming decomposed as it is the case with metal chlorides. Particularly stable are the phosphonium salts, which remain chemically inaltered during the reaction of the feed materials and also during distillation of the thiophosphonic acid dichloride. As a result, it is possible for the distillation residue to be recycled and used again in the next following reaction. In a test series made on 19 batches, where the distillation residue was recycled in each case, the catalytic activity could not be found to have decreased, so that the catalyst added once can reasonably be assumed to be useful in even a considerably larger number of reaction cycles. In other words, the present process with the use of relatively costly catalyst therein can be carried out under commercially more attractive conditions than the prior art methods, after a few reaction cycles. In addition to this, less distillation residue is obtained which means less expensive work-up or disposal.

The alkyl and arylthiophosphonic acid dichlorides made by the process of this invention are obtained in higher yields than heretofore, and they are extremely pure.

EXAMPLE 1

184 g (5.75 mols) sulfur and 1.6 g tetrabutylphosphonium bromide were introduced into a multi-necked flask provided with a stirrer, dropping funnel, reflux condenser and thermometer, and 577 g (4.93 mols) methyldichlorophosphane was added dropwise with agitation at 140° to 150° C. After a post-reaction period of 30 minutes at 150° C., methanethiophosphonic acid dichloride was distilled off from the reaction mixture at atmospheric pressure, after separation of first runnings.

The distillation residue was admixed with further sulfur and the first runnings of the first batch, and methyldichlorophosphane was added dropwise. In this manner, four further batches were processed and altogether 2670 g CH$_3$PCl$_2$ was reacted with sulfur to give 3356 g CH$_3$PSCl$_2$. The yield was 98.7% of the theoretical, the product having a purity of moe than 98% (n$_D^{23}$=1.5481). The distillation residue obtained at a rate of 57.5 g, corresponding to 1.7% based on the quantity of product, contained the catalyst of inaltered activity, which could be used in further batches.

EXAMPLE 2

192 g (6 mols) sulfur and 1.5 g tetramethylphosphonium chloride were introduced into an apparatus as described in Example 1. Next, 585 g (5 mols) CH$_3$PCl$_2$ was added dropwise to the mixture at about 150° C. and the reaction initiated. After a post-reaction period of 15 minutes, the crude product was distilled and 3 to 5 weight %, based on the total quantity, first runnings were obtained. Methanethiophosphonic acid dichloride with a purity of 99.5% was obtained in a yield of 636 g. The first runnings and distillation residue were used in another batch.

In this manner, 18 batches were processed without any intermediary addition of fresh catalyst. After altogether 19 batches, the test series was interrupted; the catalyst activity could not be found to have been reduced.

Altogether 13 871 g methanethiophosphonic acid dichloride with a purity of 99.5% was obtained in a yield of 98.0% of the theoretical.

After 19 batches, 165 g or 1.2%, based on the product quantity, distillation residue was obtained.

EXAMPLE 3

256 g (8 mols) sulfur and 1.5 g tetrabutylammonium chloride was introduced into an apparatus as described in Example 1 and 910 g (7.78 mols) methyldichlorophosphane was added dropwise with agitation at about 140° to 150° C. After a post-reaction period of 15 minutes at 150° C., first runnings were separated and 1025 g methanethiophosphonic acid dichloride was distilled off from the reaction mixture. The dichloride had a purity of more than 98%. The distillation residue was suitable for use in further batches.

EXAMPLE 4

74 g (2.31 mols) sulfur and 1.6 g tetrabutylphosphonium bromide were introduced into an apparatus as described in Example 1 and 272 g (2.08 mols) ethyldichlorphosphane was added dropwise with agitation at about 160° C. The reaction mixture was allowed to undergo post-reaction over a period of 30 minutes at 160° C. Under a reduced pressure of about 95 millibars, the reaction mixture was first freed distillatively from first runnings. Next, ethanethiophosphonic acid dichloride was distilled off at a head temperature of 92° to 94° C. 280 g dichloride with a purity of 98.1% and a refractive index n$_D^{22}$=1.5406 was obtained.

By recycling the first runnings and distillation residue, it was possible considerably to increase the yield.

EXAMPLE 5

40 g (1.25 mols) sulfur and 2 g tetrabutylphosphonium bromide were introduced into an apparatus as described in Example 1 and 210 g (1.17 1 mols) C$_6$H$_5$PCl$_2$ was added dropwise to the mixture with agitation at about 160° C. After a post-reaction of 30 minutes at 160° C., the mixture was distilled under vacuum of 4 millibars. 212 g benzenethiophosphonic acid dichloride with a purity of 99.6% and a refractive index n$_D^{22}$=1.6230 was obtained.

By recycling the first runnings and distillation residue, it was possible considerably to increase the yield.

COMPARATIVE EXAMPLE 1

In an apparatus as described in Example 1, altogether 11 561 g (98.8 mols) methyldichlorophosphane was reacted batchwise with 3 162 g (98.8 mols) sulfur with the addition of altogether 139.5 g aluminium chloride as catalyst, the reaction being effected at 140° to 150° C. 14 154 g methanethiophosphonic acid dichloride with a purity of more than 98% and n$_D^{22}$=1.5488 was distilled off from the reaction mixture. The yield was 96.1% of the theoretical and 550 g (3.9%, based on the product quantity) distillation residue was obtained.

A comparison of the test data of Example 2 and comparative Example 1 show that the present process compares favorably with prior art methods.

|  | Example 2 | Comparative Example 1 |
|---|---|---|
| Product quantity | 13 871 g | 14 154 g |
| Catalyst quantity | 1.5 g (CH$_3$)$_4$PCl | 139.5 g AlCl$_3$ |
| Distillation residue | 165 g | 550 g |
| Yield | 98% of theoretical | 96.1% of theoretical |

COMPARATIVE EXAMPLE 2

1259 g (39.3 mols) sulfur and 4599 g (39.3 mols) methyldichlorophosphane were introduced into an apparatus as described in Example 1 and reacted therein at 140° to 150° C. with addition of 28 g AlCl$_3$ as a catalyst. Methanethiophosphonic acid dichloride was distilled off from the reaction mixture and the distillation residue was then admixed with 1074 g sulfur without addition of fresh AlCl$_3$. After the addition of 1200 ml CH$_3$PCl$_3$, spontaneous strong reflux of unreacted CH$_3$PCl$_2$ set in, which reacted very reluctantly only. This phenomenon was attributable to the decreasing activity of the catalyst. 20 g fresh AlCl$_3$ was added and the reaction was terminated.

We claim:

1. In the process for making alkyl or arylthiophosphonic acid dichlorides by reacting alkyl or aryldichlorphosphanes with at least stoichiometric proportions of sulfur at a temperature above the melting point of sulfur and in the presence of a catalyst, and separating the resulting alkyl or arylthiophosphonic acid dichloride from the reaction mixture after the reaction is terminated, the improvement which comprises: effecting the reaction at a temperature between the melting point of sulfur and the boiling point of the resulting alkyl or arylthiophosphonic acid dichloride and in the presence of a catalyst of the following general formula I or II

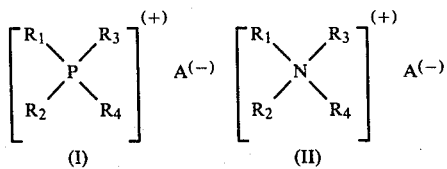

in which $R_1$, $R_2$, $R_3$ and $R_4$ stand for identical or different alkyl, aryl, alkaryl or aralkyl groups having from 1 to 22 carbon atoms and A stands for the anionic group of an organic or inorganic acid, the catalyst being used in a proportion of 0.01 up to 5 weight %, based on the quantity of the phosphane component; terminating the reaction and separating the alkyl or arylthiophosphonic acid dichloride from the reaction mixture; and using resulting catalyst-containing residue in further reactions of alkyl or aryldichlorophosphanes with sulfur.

2. The process as claimed in claim 1, wherein the alkyl or aryldichlorophosphanes as well as the alkyl or arylthiophosphonic acid chlorides contain 1 to 8 carbon atoms.

3. The process as claimed in claim 1, wherein the reaction is effected at a temperature of 130° to 170° C.

4. The process as claimed in claim 1, wherein the catalyst is selected from a tetralkylammonium or tetralkylphosphonium chloride, bromide, sulfate, nitrate or acetate.

5. The process as claimed in claim 1, wherein methyl, ethyl or phenyldichlorophosphane is used as the feed phosphane.

6. The process as claimed in claim 1, wherein the phosphane component is added portionwise to a mixture of sulfur and catalyst and, after the phosphane addition is complete, the reaction mixture is allowed to undergo post-reaction over a period of 5 to 60 minutes.

7. The process as claimed in claim 1, wherein the catalyst is used in a proportion of 0.05 to 2 weight %.

* * * * *